United States Patent [19]

Meyers

[11] 4,131,623
[45] Dec. 26, 1978

[54] SYNTHESIS OF ALDEHYDES AND PRODUCTS OF SUCH SYNTHESIS

[75] Inventor: Albert I. Meyers, New Orleans, La.

[73] Assignee: Board of Supervisors of Louisiana State University and Agricultural & Mechanical College, Baton Rouge, La.

[21] Appl. No.: 840,062

[22] Filed: Jul. 8, 1969

[51] Int. Cl.$^2$ ............................................. C07C 47/02
[52] U.S. Cl. ............................................. 260/601 R
[58] Field of Search .................. 260/601, 598, 244 R, 260/601 R

[56] References Cited

PUBLICATIONS

Meyers et al., Journ. of the Amer. Chem. Soc., vol. 91, pp. 763–767, Jan., 1969.
Tamayo, et al., Chem. Ber., vol. 97, pp. 2244–2250, 1964.
Cram et al., Organic Chemistry, 2nd Edit., pp. 261–262, 1964.

Primary Examiner—James O. Thomas, Jr.
Assistant Examiner—Werren B. Lone
Attorney, Agent, or Firm—Ostrolenk, Faber, Gerb & Soffen

[57] ABSTRACT

The disclosure describes the production of complex aliphatic, unsaturated and cycloalkane aldehydes utilizing heterocyclic ring compounds, such as oxazines, particularly dihydro-1,3-oxazines. The oxazines are treated with an alkali metal-alkane compound, such as butyl lithium in the presence of an organic solvent at subzero temperature to form an anion of the oxazine. This anion is then alkylated in the anhydrous reaction mixture by introduction of a suitable halide, epoxide or ketone while still at a subzero temperature and mixture is permitted to warm up to room temperature, following which the reaction mixture is acidified, as with hydrochloric acid to pH 2 to 3, extracted and then made basic, as with caustic alkali with cooling.

The reaction mixture is then extracted, as with ether, to produce after evaporation the alkylated dihydro-1,3-oxazine.

The alkylated dihydro-1,3-oxazine is then reacted with an alkali metal or sodium borohydride or borodeuteride or borotritide, with cooling to subzero temperatures at about a neutral pH and then transferred into a basic aqueous environment following extraction of the aqueous layer with an organic solvent, such as ether, to give a tetrahydro-1,3-oxazine. This compound may then be converted to the aldehyde desired by steam distillation or by hydrolysis in the presence of a dilute or weak acid, such as hydrochloric or oxalic acid. The aldehydes may then be extracted.

These aldehydes are useful as components or intermediates in flavoring or perfumes, in insect attractants and repellants, and in pharmaceuticals.

8 Claims, No Drawings

SYNTHESIS OF ALDEHYDES AND PRODUCTS OF SUCH SYNTHESIS

DESCRIPTION OF THE INVENTION

The present invention relates to a process for the production of aldehydes, and particularly for the production of aldehydes from oxazines. Although not limited therero, the present invention will be particularly directed to the formation of aldehydes and their C-1 deuterated derivatives from dihydro-1,3-oxazines.

The present invention is also directed to the production of novel aldehydes produced by these procedures.

It is among the objects of the present invention to provide a novel procedure for producing aldehydes, particularly useful for flavors, perfumes, insect attractants and repellants and the like, which have not been previously readily preparable.

Another object is to provide the production of novel deutero aldehydes, as well as those in which the hydrogen has been substituted by tritium.

A further object is a novel method of producing cycloalkane carboxaldehydes.

Another object is to provide a novel method of producing alpha, beta-disubstituted propionaldehydes and other related aliphatic aldehydes and their deuterated or tritio derivatives.

Another object is to provide a novel method of preparing gamma hydroxyaldehydes and their gamma oxoderivatives.

Another object is to provide a method for producing alpha, beta, unsaturated aldehydes and their deutero or tritio derivatives.

Another object is to provide a method for producing alpha, beta, gamma, delta and further conjugated unsaturated aldehydes and their deutero or tritio derivatives.

Still further objects and advantages will appear in the more detailed description set forth below, it being understood, however, that this more detailed description is given by way of illustration and explanation only and not by way of limitation, since various changes therein may be made by those skilled in the art without departing from the scope and spirit of the present invention.

In accomplishing the above objects, it is usually desirable to start with dihydro-1,3-oxazines and particularly the trialkylated oxazine. The first step consists of treating this oxazine with an alkali metal substituted alkane group in the presence of an organic solvent in anhydrous condition, so that alkali metal salt is produced of 2-alkyl, or 2-benzyl dihydro-1,3-oxazine.

A typical starting compound may be 2,4,4,6-tetramethyl-5,6-dihydro-1,3-(4H)-oxazine, and, in lieu of the methyl groups, there may be various substituents, including ethyl, propyl or butyl groups, and in lieu of the hydrogen at the 2-carbon position, other groups, such as phenyl or carboethoxy may be used.

This oxazine is converted quantitatively into an alkali metal salt, such as a lithium salt, at a temperature below −50° C by reaction with phenyl, n-butyl, or tertiary butyl lithium. These are dissolved in an organic solvent, such as tetrahydrofuran. The anion which is produced will remain stable below −50° C for several days or longer.

A typical reaction of this type may be set forth:

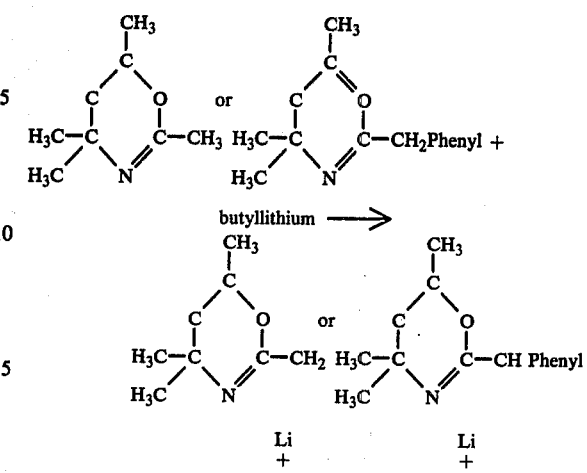

To this anion reaction mixture is then discharged an electrophile, which may be a halide or epoxide or ketone, slowly over a period of about thirty minutes. The reaction mixture is then allowed to warm up to room temperature and the mixture is then poured into cold water and acidified with hydrochloric acid. The resulting solution is extracted with ether, pentane or a dichloromethane and the extract discarded. The aqueous solution is neutralized with alkali and the resulting material is extracted with ether. The ether is removed to give a crude alkylated dihydro-1,3-oxazine and a yield of 90 to 98%.

The alkylated dihydro-1,3-oxazine is then reduced. In this third step, the reaction mixture containing the crude alkylated oxazine and also containing tetrahydrofuran is cooled to subzero temperature, between zero and −50° C, and hydrochloric acid is added to give a pH of about 7. Then an alkali metal borohydride solution in particular sodium or potassium borohydride solution is added to the reaction mixture, while maintaining a pH of 6 to 8.

After the addition of the borohydride solution, the reaction mixture is poured into water, followed by the addition of sodium hydroxide. The aqueous solution then is extracted with ether and when the ether is evaporated, there remains crude tetrahydro-oxazine in a yield of over 90%.

The next step is to convert the tetrahydro-oxazine to the aldehyde and this is preferably done by steam distillation or by hydrolysis.

With steam distillation, the tetrahydro-oxazine is added drop-wise to the solution of oxalic acid in water or dilute aqueous mineral acid over a period of about twenty minutes. The steam distillation is continued until the distillate is free from all organic material. The distillate then may be extracted with an organic solvent, such as pentane or ether, to give the pure aldehyde.

If the aldehyde is water soluble or insufficiently volatile to make steam distillation practical, the oxazine may be added directly to the oxalic acid solution and refluxed and then extracted with ether, pentane, or a chlorinated alkane.

Among the typical aldehydes that may be produced by this procedure are

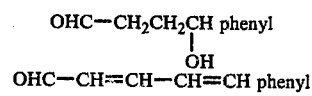

-continued

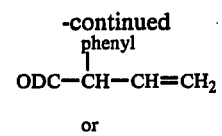

or an alkylated or phenyl derivative of an alicyclic or heterocyclic ring containing an aldehyde group.

EXAMPLE I (a) Preparation of anion of 2-alkyl or alkylene (1 to 12 carbon atoms), particularly 2-methyl or 2-benzyl dihydro-1, 3-oxazine A 500 ml (milliliter) three-necked flask equipped with a magnetic stirring bar, a 75 ml addition funnel topped with a rubber septum, and a nitrogen inlet tube is successively evacuated and flushed with nitrogen. An anhydrous tetrahydrofuran (100 ml) solution of 14.1 grams (0.10 mole) of 2,4,4,6-tetramethyl-4,5-dihydro-1,3-oxazine are added from a syringe through the rubber septum. 2-benzyl-4,4,6-trimethyl-5,6-dihydro-1,3-oxazine, 2,4,4,6-tetramethyl-5,6,-dihydro-1,3-oxazine, 2-carboethoxy-4,4,6-trimethyl-5,6-dihydro-1,3-oxazine, 2-cyanomethyl-4,4,6-trimethyl-5,6-dihydro-1,3-oxazine, 2-methyl-4,4,6-triethyl-5,6-dihydro-1, 3-oxazine, or 2-benzyl-4,6-dimethyl-4-ethyl-5,6-dihydro-1, 3-oxazine may be used together with or in lieu of the oxazine above set forth.

The solution while being stirred is cooled to below −50° C and desirably between −60° C and −90° C in a dry ice organic solvent (acetone) bath and 69.0 ml (0.11 mole, preferably in the form of a 1.6 molar solution) of normal or tertiary butyllithium dissolved in an organic solvent (hexane) is injected slowly into the addition funnel. The butyllithium solution is added drop-wise over a period of one hour. Approximately one hour after the addition is complete a yellow salt precipitate forms. The use of tertiary-butyllithium in place of normal butyllithium will generate the salt quickly, resulting in the precipitation in a few minutes, thus shortening the procedure by several hours. A complete salt formation is accomplished. The salt may not precipitate if higher than the above quantity of solvents is employed.

(b) Alkylation of Anion

An electrophile in the amount of 0.11 mole of an alkyl, alkenyl or aralkyl (1 to 26 carbon atoms) halide epoxide, aldehyde or ketone, in 25 ml of anhydrous organic solvent, such as tetrahydrofuran is injected into the additional funnel and is slowly added to the mixture over a period of about twenty to sixty minutes. The reaction mixture is allowed slowly to warm to room temperature by which time the yellow precipitate disappears. The mixture is then poured into about 100 ml of ice water and acidified to pH 2 to 3 with 9 N hydrochloric acid. This acid solution is extracted with three 75 ml portions of pentane and the aqueous solution is made basic (pH 7 to 9) by the careful addition of 40% sodium hydroxide aqueous solution.

Ice is added to keep the mixture cool during the neutralization. The resulting oil is extracted with three 75 ml portions of ether and the ether extracts are dried by anhydrous potassium carbonate. The ether is removed by rotary evaporation to give the alkylated dihydro-1,3-oxazone in a yield of 90 to 98%.

(c) Reduction of the dihydro-1,3-oxazine

To a 600-ml beaker is added 100 ml of tetrahydrofuran, 100 ml of 95% ethyl alcohol, and the crude dihydrooxazine obtained in the preceding experiment I (b). The mixture is cooled between −35 and −40° C, with an acetone bath to which dry ice is added as needed. Hydrochloric acid (9 N) is added to the magnetically stirred solution until an approximate pH of 7 is obtained.

Sodium borohydride (or sodium borodeuteride) solution is prepared by dissolving 3.78 g (0.10 mole) in a minimum amount of water (about 4 to 5 ml) to which one drop of 40% sodium hydroxide is added. The sodium borohydride solution and the 9N hydrochloric acid solution are added to the stirred solution alternately so that a pH 6 to 8 is maintained. The acid and hydride solutions from two 50 ml burets are placed above the beaker. The pH is monitored by periodic checks with pH paper.

During the addition care is taken to maintain a temperature between −35 and −45° C. After addition of this borohydride solution is complete, the solution is stirred with cooling for an additional hour (pH 7 is maintained by the occasional addition of hydrochloric acid solution).

The contents are then poured into about 100 ml of water and made basic by the addition of 40% sodium hydroxide solution. The layers are separated and the aqueous solution is extracted with three 75 ml portions of diethylether. The combined organic extracts are washed with 100 ml of saturated sodium chloride solution and dried by anhydrous potassium carbonate. The ether is removed by rotary evaporation to give the crude tetrahydrooxazine in a yield of 90 to 99%.

(d) Cleavage of the tetrahydrooxazine to the aldehyde (e) A steam distillation

To a 250 ml flask equipped with a distillation head and an addition funnel with a nitrogen tube, is added 50.4 g (0.40 mole) of hydrated oxalic acid and about 150 ml of water. Steam is introduced into the solution and the tetrahydrooxazine (about 0.1 mole) is slowly added drop-wise over a period of twenty minutes.

The addition funnel is then washed down with 5 ml of one molar oxalic solution. The steam distillation is continued until the distillate is free of organic material. The distillate is extracted with three 50 ml portions of pentane or ether. The extracts are dried by anhydrous sodium sulfate and the solvent removed to give the pure aldehyde. In some instances distillation of the product may be necessary.

(f) Hydrolysis

In cases where the aldehyde is water soluble or is insufficiently volatile to make steam distillation practical, the following procedure is used. In this procedure for isolation any of the aldehydes prepared by this method is quite satisfactory since steam distillation, in many instances requires prolonged heating, consuming considerable time. However, certain acid sensitive aldehydes (i.e., cyclopropane and phenylcyclopropane carboxaldehydes) are best isolated by steam distillation since their contact time in the acid medium is minimized. The crude tetrahydro-1,3-oxazine (0.1 mole) is added to the oxalic acid solution prepared above and heated to reflux for two hours. The cloudy solution is extracted with ether, pentane, or dichloromethane (depending on the nature of the aldehyde) and the extracts washed with 5% sodium bicarbonate solution, and dried Concentration of the solution is followed by either distillation or recrystallization.

EXAMPLE II

Preparation of Cycloalkane Carboxaldehydes

To a 500-ml three-necked, round-bottom flask equipped with a nitrogen inlet tube, a rubber septum and a magnetic stirrer, is added 250 ml tetrahydrofuran and 10.9 g (0.05 mole) of 2-benzyl-4,4,6-tetramethyl-4,5-dihydro-1,3-oxazine. The mixture is cooled to −78° C and 32.0 ml (0.06 mole, 1.6 M) normal butyllithium in hexane is slowly added.

After one hour of stirring, 11.5 g (0.05 mole) of 1,4-dibromobutane is added and allowed to react for 0.5 hour. Normal butyllithium (0.06 mole) is added and the mixture is allowed to slowly warm to −50° C and maintained at that temperature for two hours. The mixture is then poured into 150 ml of water and crushed ice, acidified to pH 2 to 3, and is extracted with ether. The ether extract is discarded.

The aqueous solution is basified with 40% sodium hydroxide and extracted with ether. The ether extract is dried over potassium carbonate and the solvent removed by rotary evaporation to give a 90 to 97% yield.

When the 2-methyl oxazine is employed, the cyclization step is carried out using two equivalents of butyllithium since yields are found to be generally lower when only one equivalent is employed.

The reduction and cleavage of the oxazine to the cycloalkane carboxaldehyde is performed using the procedure given in Example I.

EXAMPLE III

4-Hydroxy-3-phenylbutanal was prepared according to the procedures in Example I using 35.5 g (0.25 mole) of the 2-methyloxazine, 164 ml (0.26 mole) normal butyllithium, and 31.3 g (0.26 mole) styrene oxide. There was obtained 26.6 g (65%) of the butanal after hydrolysis and extraction from the oxalic acid solution. The sample may be further purified by elution through neutral alumina using pentane.

The product was also observed to be a mixture of cis and trans isomers. A 2,4-dinitrophenylhydrazone derivative was readily prepared, having a melting point of 106°-107° C.

EXAMPLE IV

5-Phenyl 2,4-pentadienal was prepared according to the procedure of Example I, using 35.5 g (0.25 mole) of the 2-methyloxazine, 170 ml (0.26 mole) normal butyllithium and 36.3 g (0.27 mole) cinnamaldehyde. The product was isolated by extraction (dichloromethane) of the oxalic acid solution after 1.5 hours reflux. The crude yield was 38.8 g (71%) of a tan colored solid. Recrystallization from pentane gave an analytically pure sample, mp 41° C. The product is kept intact by storage in the freezer under nitrogen.

EXAMPLE V

1-Deutero-2-phenyl-4-pentanal was prepared according to the procedure of Example I, using 21.7 g (0.10 mole) of 2-benzyl-4,4,6-tetramethyl-4,5-dihydro-1,3-oxazine, 48 ml (0.11 mole) normal butyllithium, and 12.1 g (0.10 mole) allyl bromide. A 21.0 g (0.08 mole) sample of the oxazine thus produced was reduced with 3.7 g (0.09 mole) of sodium borodeuteride. The pentanal product was obtained in 70% overall yield by cleavage of the tetrahydro-1,3-oxazine derivative in oxalic acid solution (2 hours reflux). The pentanal was then obtained by fractional distillation at 64° to 65° C under a pressure of 0.3 mm.

EXAMPLE VI

Production of 1-Phenylcyclopentane Carboxaldehyde

In starting the procedure, to a 250 ml (3-necked, round bottom) flask equipped with a nitrogen inlet tube, a rubber septum and a magnetic stirrer is added 100 ml tetrahydrofuran solution of 5.64 g (0.04 mole) of 2,benzyl-4,4,6-tetramethyl-4,5-dihydro-1,3-oxazine. The mixture is cooled to −78° C and 0.044 mole of normal butyllithium disssolved in hexane is slowly added.

After three hours, 0.044 mole of an alkyl dihalide having 1 to 12 carbon atoms is added and allowed to react for 0.5 hour. The dihalide may also be 1-bromo-2-chloroethane;
1,3-dibromopropane;
1,4-dibromobutane; or 1,5-dibromopentane;
1,2-dibromoethane; or 1,6-dibromohexane.

Normal butyllithium (0.08 mole) is again added and the mixture is allowed to slowly warm to −50° C and maintained at that temperature for three hours.

The mixture is then poured into 100 ml of cold 3N hydrochloric acid and extracted with hexane. The aqueous solution is basified with 40% NaOH and extracted with ether. The ether extract is dried over $K_2CO_3$ and the solvent removed by rotary evaporation.

The reduction and cleavage of the oxazine are the same as described in Example I.

The aldehyde was obtained in 60% overall yield by steam distillation from oxalic acid solution in semi-solid state.

EXAMPLE VII

Synthesis of Gamma-Hydroxyaldehydes and their Gamma-Oxoderivatives from Dihydro-1,3-Oxazines The lithio salt of the oxazine is used as nucleophile in the reaction with alkyl halides and carbonyl compounds producing ultimately acyclic, alicyclic, and alpha, beta unsaturated aldehydes and their C-1 deuteriated derivatives. At the same time the reaction of the oxazine with unsaturated alkyl epoxides (ethylene, styrene, and cyclohexene) will produce precursors to gamma-hydroxyaldehydes and their oxoderivatives by use of sodium borohydride. The C-1 deuteriated derivatives may also be produced, using sodium borodeuteride in place of sodium borohydride.

Addition of the epoxides to a tetrahydrofuran solution of the lithio salt at −78° C produces pure oxazinyl carbinols which may be reduced at −35° C by sodium borohydride to yield the corresponding tetrahydro-1,3-oxazines. Cleavage or reduction in aqueous oxalic acid and recovery of the aldehyde by extraction or steam distillation produced a gamma-hydroxy derivative. The hydroxyaldehydes exist primarily as the cyclic hemiacetals. This three step sequence is a three step operation requiring no purification of the intermediates and can be accomplished in 24 to 48 hours, using the 1,3-oxazines.

The reaction product does not react with added ethyl iodide, benzoyl chloride, or ethylene oxide. The gamma-oxoderivatives, for example ethyl, or benzoyl, were obtained by treating oxazinyl carbinol produced with sodium hydride in tetrahydrofuran at room temperature followed by the addition of the alkyl or acyl halide. Subsequent reduction and hydrolysis gave the gamma-substituted aldehydes. In this manner, 4-ethoxybutanal, and 4-benzoyloxybutanal were obtained in high yields respectively.

EXAMPLE VIII

Production of Alpha, Beta-Disubstituted Propionaldehyde 2-vinyldihydro-1,3-oxazine is used for obtaining propionaldehyde derivatives, substituted at C-2 and C-3 by alkyl, alkenyl, and aryl groups containing 1 to 12 carbon atoms.

A solution of the oxazine and an alkyl halide in tetrahydrofuran was cooled (−40 to −60° C) and treated with a Grignard reagent (ethyl magnesium halide) to produce a doubly alkylated oxazine. Reduction of the oxazine with aqueous sodium borohydride or deuteride at −35° C produced the tetrahydro derivative, which was directly converted to the alpha, beta-disubstituted propionaldehyde by hydrolysis in aqueous oxalic acid. The pure aldehyde was produced by either extraction or steam distillation.

EXAMPLE IX

Preparation of -2-methyl-3-phenylpropanal (a) A solution containing 10.0 g (0.06 mole) of 2-vinyl-4,4,6-trimethyl-5,6-dihydro-1,3-4H-oxazine, 6.1 ml (0.09 mole) methyl iodide, and 100 ml tetrahydrofuran is cooled to −60° (dry ice-acetone) under nitrogen. To the stirred solution, 51 ml (0.15 mole, 3.0 M) of ethereal phenylmagnesium bromide (Grignard reagent) is added dropwise over a period of 30 minutes.

The reaction mixture is stirred after complete addition for 1 hour at −60° to −65° and then slowly allowed to warm to room temperature. The excess Grignard reagent is decomposed by the careful addition of 10 ml water and the contents of the flask are poured into 200 ml of an ice-water mixture. The solution is acidified with dilute hydrochloric acid (pH 2-3) and then extracted with three 75 ml portions of petroleum ether.

The latter extracts are discarded and the aqueous solution is rendered alkaline by the addition of 40% sodium hydroxide solution. The oil that appears is removed by extraction with three 100 ml portions of ether and the extracts dried over potassium carbonate. Concentration of the ethereal extracts provides 14.8 g (93%) yield of the dialkylated oxazine. The dialkylated oxazine shows strong absorption at 1665 cm$^{-1}$ (C=N).

(b) Borohydride Reduction: The C=N link is reduced to the tetrahydro-1,3-oxazine. The reduction is performed using 2.5 g (0.06 mole) sodium borohydride and 13.7 g (93%) of tetrahydro-1,3-oxazine is obtained. The tetrahydro-1,3-oxazine exhibited no absorption in the 1665 cm$^{-1}$ region and showed the NH band at 3270 cm$^{-1}$.

(c) Oxalic acid cleavage to the propanal

The crude tetrahydro-1,3-oxazine (13.1 g) is added dropwise to a boiling oxalic acid solution (33.4 g per 150 ml water) and the aldehyde collected in the steam distillate. Ethereal extraction (three 50 ml portions) of the distillate is followed by drying over sodium sulfate. Removal of the solvent yields 6.0 g (77%) of 2-methyl-3-phenyl-propanal in overall yield of 66%.

EXAMPLE X

Preparation of 2,4,4-trimethylpentanal (a) 2-(1 tertiary-butyl-2-propyl)-4,4,6-trimethyl-5,6-dihydro-1,3-4H-oxazine. - A solution containing 10.5 g (0.063 mole) of 2-isopropenyl-4,4,6-trimethyl-5,6-dihydro-1,3-4H-oxazine and 150 ml tetrahydrofuran was cooled to between 25° and −78° (dry ice-acetone) under nitrogen. To the stirred solution, 55.6 ml (0.069 mole, 1.24 M) of tertiary butyl lithium in pentane was added over a period of 30 minutes. The reaction mixture was stirred after complete addition for 1 hour at −78° and then quenched with water.

The solution was acidified with dilute hydrochloric acid (pH 2-3) and then extracted with three 75 ml portions of pentane. The latter extracts were discarded and the aqueous solution was rendered alkaline by the addition of 40% sodium hydroxide solution. The aqueous solution was extracted with three 100 ml portions of diethyl ether and the extracts were dried over potassium carbonate. Concentration of the ethereal extracts gave 13.3g (95%) of crude 2-(1 t-butyl-2-propyl)-4,4,6-trimethyl-5,6-dihydro-1,3-4H-oxazine. The product when distilled had a bp 110°-113°/25 mm and a mass spectrum of 225.

(b) Borohydride reduction of 2-(1 tertiary-butyl-2-propyl)-4,4,6-trimethyl-5,6-dihydro-1,3-4H-oxazine.

The reduction was performed using 12.0 g (0.053 mole) of crude 2-(1-tertiary-butyl-2-propyl)-4,4,6-trimethyl-5,6-dihydro-1,3-4H-oxazine, an equivalent volume of tetrahydrofuran and 95% ethanol, and 2.0 g(0.053 mole) sodium borohydride solution (in water). A pH of 6-8 was maintained by the alternate addition of the sodium borohydride solution and 9N hydrochloric acid solution at a temperature between −35 and −45° C.

After addition of the borohydride solution was complete, the solution was stirred with cooling for an additional hour and then allowed to warm up to −20° during 1 hour.

The contents were then poured into approximately 100 ml of water and made basic by the addition of 40% sodium hydroxide solution. The aqueous solution was extracted with 75 ml portions of diethylether. The combined organic extracts were washed with 100 ml of saturated sodium chloride solution and dried over anhydrous potassium carbonate. Concentration of the ethereal extracts gave 11.7 g(97%) of crude tetrahydro-1,3-oxazine.

(c) Production of 2,4,4-trimethylpentanal

A solution of 11.4 g (0.051 mole) of crude tetrahydro-1,3-oxazine, 100 ml of water, and 32.0 g (0.25 mole) of hydrated oxalic acid was heated at reflux temperature for 2 hours. The solution was cooled to room temperature and extracted with three 50 ml portions of diethyl ether. The ethereal extracts were washed with aqueous sodium bicarbonate solution and then dried over anhydrous sodium sulfate. The solvent was removed and the residue was distilled.

There was obtained 3.1 g (48%) of 2,4,4-trimethylpentanal, boiling point 44°-46°/26 mm. The overall yield of aldehyde, based on the starting dihydrooxazine, was 42.0%.

EXAMPLE XI

3-cyclohexyl-2-methylpropanal (a) Production of 2-(1-cyclohexyl-2-propyl)-4,4,6-trimethyl-5,6-dihydro-1,3-4H-oxazine A solution containing 9.9 g (0.059 mole) of 2-isopropenyl-4,4,6-trimethyl-5,6-dihydro-1,3-4H-oxazine and 150 ml tetrahydrofuran was cooled to −60 to −65° (dry ice-acetone) under nitrogen. To this stirred solution, the Grignard solution prepared from 23.4 ml (0.19 mole) cyclohexylbromide and 5.6 g (0.23 mole) magnesium (triply sublimed) in 75 ml diethylether was added over a period of 30 minutes. The reaction mixture was allowed to warm up to room temperature overnight and then water was added.

The solution was acidified with dilute hydrochloric acid (pH 2-3) and then extracted with three 75 ml portions of pentane. The latter extracts were discarded and the aqueous solution was rendered alkaline by the addition of 40% sodium hydroxide solution.

The aqueous solution was then extracted with three 100 ml portions of diethyl ether and the extracts were dried over potassium carbonate. Concentration of the ethereal extracts gave 14.5 g (98%) of crude 2-(1-cyclohexyl-2-propyl)-4,4,6-trimethyl-5,6-dihydro-1,3-4H-oxazine.

(b) Borohydride reduction of 2-(1-cyclohexyl-2-propyl)-4,4,6-trimethyl-5,6-dihydro-1,3-4H-oxazine The reduction was performed using 14.4 g (0.057 mole) of crude 2-(1-cyclohexyl-2-propyl)-4,4,6-trimethyl-5,6-dihydro-1,3-4H-oxazine, an equivalent volume of tetrahydrofuran and 95% ethanol, and 2.2 g (0.057 mole) sodium borohydride solution (in water).

A pH 6-8 was maintained by the alternate addition of the sodium borohydride solution and 9N hydrochloric acid solution at a temperature between −35° and −45°. After addition of the borohydride solution was complete, the solution was stirred with cooling for an additional hour and then allowed to warm up to −20° (1 hour). The contents were then poured into approximately 100 ml of water and made basic by the addition of 40% sodium hydroxide solution. The aqueous solution was extracted with three 75 ml portions of diethylether. The combined organic extracts were washed with 100 ml of saturated sodium chloride solution and dried over anhydrous potassium carbonate. Concentration of the ethereal extracts gave 14.1 g (97.1%) of crude tetrahydro-1,3-oxazine.

(c) Production of 3-cyclohexyl-2-methylpropanal

A solution of 13.7 g (0.054 mole) of crude tetrahydro-1,3-oxazine, 100 ml of water, and 34,3 g (0.27 mole) of hydrated oxalic acid was heated at reflux temperature for 2 hours. The solution was cooled to room temperature and extracted with three 50 ml portions of diethyl ether. The ethereal extracts were washed with aqueous sodium bicarbonate solution and then dried over anhydrous sodium sulfate.

The solvent was removed and the residue was distilled. There was obtained 6.9 g (83%) of 3-cyclohexyl-2-methylpropanal, boiling point 106°-109°/25 mm. The overall yield of aldehyde, based on the starting dihydrooxazine, was 79.0%.

The following alkali metal alkanes may be used in addition to or in lieu of those set forth in the above examples:

| | |
|---|---|
| ethyl (lithium, sodium, potassium); | butyl (lithium, potassium |
| propyl (lithium, sodium, potassium); | sodium hydride |
| methyl (lithium, sodium, potassium); | sodium dimethylsulfinate |
| octyl (lithium, sodium, potassium); | sodium or potassium amides |
| hexyl (lithium, sodium, potassium); dialkylamides (alkyl=methyl, ethyl, propyl, butyl) | sodium or potassium |

The following solvents may be used in addition to or in lieu of those set forth in the above examples:

ether, tetrahydrofuran, 1,2-dimethoxyethane, polyglycol ethers, pentane, hexane, benzene, or dimethyl sulfoxide The following electrophiles may be used in addition to or in lieu of those set forth in the above examples:

(a)

alkyl and aralkyl ($C_1$ to $C_{20}$) halides
alkyl ($C_1$–$C_{20}$) iodides and bromides
cycloalkyl ($C_3$–$C_{10}$) iodides and bromides
alkane dihalides ($C_2$–$C_{10}$), the halides being chlorides, bromides or iodides or mixtures
unsaturated alkyl ($C_3$–$C_{20}$) iodides and bromides
allylic ($C_3$–$C_{20}$) iodides, bromides and chlorides
phenyl or naphthylalkyl ($C_1$–$C_{20}$) iodides and bromides
cyano, ester, and ether containing halides of the above classes (b)

dialkyl ($C_1$–$C_{20}$) ketones
heterocyclic (pyridine, pyrrole, thiophene, furan) ketones
diaryl (phenyl, napthyl) ketones
aryl (phenyl, napthyl) alkyl ($C_1$–$C_{20}$) ketones
cycloalkyl ketones ($C_3$–$C_{10}$)
alkyl ($C_1$–$C_{20}$) aldehydes
aryl (phenyl, naphthyl, phenanthryl, anthracenyl) aldehydes
cycloalkyl ($C_3$–$C_{10}$) aldehydes
heterocyclic (pyridines, pyrrole, thiophene, furan) aldehydes
$\alpha,\beta$-unsaturated aldehydes and ketones of the above classes.

The following epoxides may be used in the above examples:

straight chain alkene ($C_2$–$C_{20}$) epoxides
branched chain alkene ($C_3$–$C_{20}$) epoxides
phenyl or naphthyl containing alkenes ($C_2$–$C_{20}$) epoxides
cycloalkene ($C_4$–$C_{10}$) epoxides
heterocyclic (pyridine, pyrrole, thiophene, furan) alkene epoxides.

The following epoxides may also be used, particularly to make gamma-hydroxyaldehydes, namely (a) styrene epoxide; (b) cyclo-hexene epoxide; and (c) ethylene epoxide.

Among the oxazines that may be used are:
(a) 2-methyl, 2-ethyl, 2-butyl or 2-propyl oxazines (b) 2-carboethoxy, 2-carbopropoxy, or 2-carbobutoxy oxazines
(c) 2 cycloalkyl tetrahydro-1,3-oxazines
(d) bromo-, chloro, or iodo-alkyl-1,3-oxazines
(e) 2-carbethoxyl alkyl (methyl, ethyl or butyl),
(f) vinyl oxazines by reacting acrylonitrile and 2,4-pentanediol. These vinyl oxazines may be reacted with Grignard reagents in the presence of alkyl, allyl, and benzyl halides and epoxides.

The overall general equation is as follows:

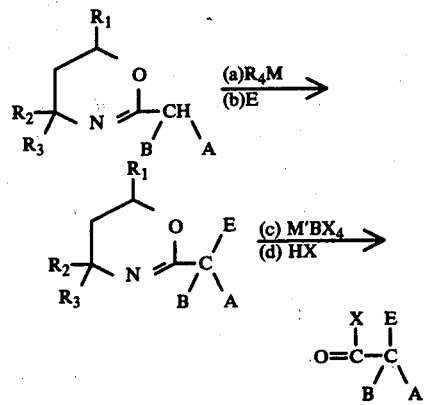

(Equation A)

$R_1 = R_2 = R_3 =$ Hydrogen, methyl, ethyl, propyl
$R_4 =$ methyl, ethyl, propyl, butyl, phenyl, dimethylsulfinyl
$M =$ lithium, sodium, potassium
$A = B =$ hydrogen, phenyl, cyano, methoxy, carboalkoxy
$E =$ alkyl, aralkyl, cycloalkyl as bromide, chloride, or iodide, dialkyl, diaryl, alkylaryl ketones alkyl, aryalkyl, cycloalkyl carboxaldehydes alkene epoxides, the alkyl and alkene groups having 2 to 12 carbon atoms and the aryl groups being phenyl tolyl, xylyl, napthyl or anthracyl
$M' =$ sodium, potassium
$BX_4^- = BH_4^-, BD_4^-, BT_4^-$ (hydrogen, deuterium, tritium)
$HX =$ acetic, propionic, benzoic, oxalic, hydrochloric, hydrobromic acids.

The aldehydes which may be prepared are: (In every case in the CHO aldehyde group, deuterium or tritium may be substituted for hydrogen).

(a) acetaldehyde ($C_2$)
(b) propionaldehyde ($C_3$)
(c) butyroaldehyde ($C_4$)
(d) valeraldehyde ($C_5$)
(e) caproaldehyde ($C_6$)
(f) heptaldehyde ($C_7$)
(g) octaldehyde ($C_8$)
(h) nonaldehyde ($C_9$)
(i) decaldehyde ($C_{10}$)
(j) undecaldehyde ($C_{11}$)
(k) dodecaldehyde ($C_{12}$)
(l) $OHC-CH_2CH_2-CH_2=CH_2$ 4-pentenal (m) $OHC-CH_2CH_2-C=CH_2$ 4-methyl-4-pental
           $\phantom{OHC-CH_2CH_2-C=}CH_3$ (n) $OHC-CH_2CH_2CH_2-CH=CH_2$ 5-hexenal (o) cyclopropane carboxaldehyde
(p) cyclobutane carboxaldehyde
(q) cyclopentane carboxaldehyde
(r) cycloheptane carboxaldehyde (The cycloalkane groups of (o) to (r) may also be substituted at the carbon carrying the aldehyde by a phenyl group).

| | |
|---|---|
| s) $OHC-CH=CH-CH_3$ | $\beta$-methyl acrolein |
| $OHC-CH=C\genfrac{}{}{0pt}{}{CH_3}{CH_3}$ | $\beta,\beta$-dimethyl acrolein |
| $OHC-CH=C\genfrac{}{}{0pt}{}{C_2H_5}{CH_3}$ | $\beta$-methyl-$\beta$-ethyl acrolein |
| $OHC-CH=C\genfrac{}{}{0pt}{}{C_2H_5}{C_2H_5}$ | $\beta,\beta$-diethyl acrolein |
| $OHC-CH=C\genfrac{}{}{0pt}{}{phenyl}{phenyl}$ | $\beta,\beta$-diphenyl acrolein |
| $OHC-CH=C\genfrac{}{}{0pt}{}{phenyl}{phenyl}$ | $\beta$-methyl-$\beta$-phenyl acrolein |
| $OHC-CH=$cyclopentane | $\beta,\beta$-tetramethylene acrolein |
| $OHC-CH=$phenyl | $\beta,\beta$-pentamethylene acrolein |
| $OHC-CH=$(3-cholestyl) | $\beta,\beta$-(3-chloestylidine acrolein |
| $OHC-CH=CH-CH=CH-CH_3$ | 2,4-hexadienal |
| $OHC-CH=CH-CN=CH$-phenyl | 5-phenyl-2,4-pentadienal |
| trans-beta-ionylidene acetaldehyde (the following may also be C=C-CHO phenyl) | |
| 3-thienyl-$CH=CH-CHO$ | $\beta$(3-thienyl) acrolein |
| 3-furyl-$CH=CH-CHO$ | $\beta$-(3-furyl) acrolein |
| betapyridyl-$CH=CH-CHO$ | $\beta(\beta$-pyridyl) acrolein |
| 2-pyridyl $CH=CH-CHO$ | $\beta$(2-pyridyl) acrolein |
| quinolyl $CH=CH-CHO$ | |
| $OHC-CH_2CH_2CH_2OH$ | 4-hydroxylbutanal |
| $OHC-CH_2CHCH\genfrac{}{}{0pt}{}{phenyl}{}$ | 4-hydroxy-3-phenyl-butanal |
| $\phantom{OHC-CH_2CHCH}OH$ | |
| $OHC-CH_2$-cyclohexyl-OH | 2-hydroxyeychlohexyl-acetaldehyde |
| $OHC-CH_2$-cyclopentyl-OH | 2-hydroxycyclopental-acetaldehyde |
| $OHC-CH_2CH_2CH_2OCH_3$ | 4-methoxybutanal |
| $OHC-CH_2CH_2CH_2OCH_2$phenyl | 4-benzyloxybutanal |
| $OHC-CH_2CH_2CH_2O\underset{\underset{O}{\|}}{C}$-phenyl | 4-benzyloxybutanal |
| $OHCCH_2CH_2CH_2O\underset{\underset{O}{\|}}{C}-CH_2CH_3$ | 4-propionoxy butanal |

The general equation using the Grignard reagent is:

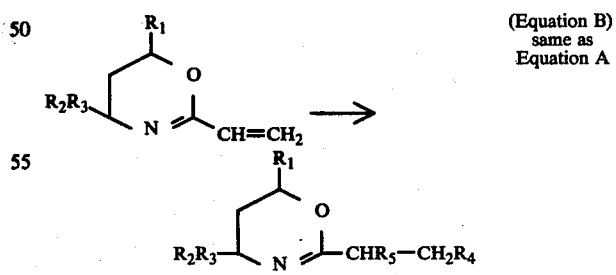

(Equation B) same as Equation A $R_1 = R_2 = R_3 =$ methyl, ethyl, propyl
$R_4 = C_1-C_{12}$ alkane
$R_5 = C_1-C_{12}$ alkane
$X =$ bromide, iodide
Temperature $-20°$ to $-60°$
Solvents - ether, tetrahydrofuran, polyglycol ethers Products prepared by this process

| | |
|---|---|
| OHC—CH—CH$_2$C$_6$H$_5$<br>    \|<br>    CH$_3$ | 2-methyl-3-phenyl propanal |
| OHC—CHCH$_2$phenyl<br>    \|<br>    CH$_2$phenyl | 2-benzyl-3-phenyl propanal |
| OHC—CHCH$_2$phenyl<br>    \|<br>    CH$_2$CH=CH$_2$ | 2-allyl-3-phenyl propanal |
| OHC—CHCH$_2$phenyl<br>    \|<br>    CH$_2$CH—phenyl<br>         \|<br>         OH | 2-benzyl-4-hydroxy-4-phenyl butanal |
| OHC—CHCH$_2$phenyl<br>    \|<br>    CH$_2$CH$_3$ | 2-ethyl-3-phenyl propanal |
| OHC—CHCH$_2$CH$_3$<br>    \|<br>    CH$_2$phenyl | 2-benzyl butanal |
| OHC—CHCH$_2$CH$_2$CH$_3$<br>    \|<br>    CH$_2$phenyl | 2-benzyl pentanal |
| OHC—CHCH$_2$CH$_2$CH=CH$_2$<br>    \|<br>    CH$_2$ phenyl | 2-benzyl-5-hexenal |
| OHC—CH—CH$_2$CH$_2$CH=CH$_2$<br>    \|<br>    CH$_2$CH=CH$_2$ | 4-formyl-1,7-octadiene aldehyde |
| OHC—C(CH$_2$)$_8$CH$_3$<br>    \|<br>    CH$_2$CH$_2$CH$_2$CH$_2$CH$_3$ | 6-formyl pentadecane aldehyde |
| OHC—CH—CH$_2$CH$_2$—$\overset{H}{\underset{\|}{C}}$—CH$_3$<br>    \|                         \|<br>    CH$_3$                   CH$_3$ | 2-methyl-5-formylhexane aldehyde |
| OHC—CH—CH$_2$—cyclohexyl<br>    \|<br>    CH$_3$ | 2-cyclohexyl-2-methyl propanal |
| OHC—CH—(CH$_2$)$_5$CH$_3$ | 2-methyloctanal |

The utility of aldehydes:

(a) citral (3,7-dimethyl-2,6-octadienal) — useful in synthesis of vitamin A, flavoring agent in perfume
(b) valeradehyde (hexanal) useful in flavoring compounds, resins, and rubber accelerators.
(c) butyraldehyde useful in rubber cements, synthetic resins.
(d) trans - 2-hexenal useful as cockroach repellent.
(e) iso-butyraldehyde useful as insect repellent, plasticizer, in perfumes and flavors.
(f) n-nonaldehyde (pelargonic aldehyde) useful as flavoring in artificial lemon oil.
(g) cinnamic aldehyde useful in perfumes, soaps and cosmetics.
(h) decyl aldehyde useful as flavoring agent; oil of orange.
(i) isovaleric aldehyde useful as flavoring for ill-tasting medicines.
(j) phenylacetaldehyde useful in perfumery.
(k) β-(3,3-dimethylcyclohexylidene) acetaldehyde useful as sex-attractant to boll weevil.

In the above examples, all of the temperatures given are in Centigrade.

The aldehyde is derived from the 2-position of the oxazine ring.

The following are additional equations setting forth the procedures of the above examples:

| | | Step 1 | Step 2 | |
|---|---|---|---|---|
| Steps 1 & 2 | [oxazine structure with R$_1$, R$_2$R$_3$, N, O, CH$_2$, A] | + alkalimetal - R$_4$ complex (sodium, potassium or lithium) | +R$_5$halide (chloride, bromide or iodide) | Equation C |
| Step 3 | [oxazine structure with R$_1$, R$_2$R$_3$, N, O, CHR$_5$, A] | + acidified aqueous alkalimetal borohydride or deuteride (sodium, potassium or lithium) | | |
| Step 4 | [oxazine structure with R$_1$, R$_2$R$_3$, N, O, H or D, CHR$_5$, A] | + dilute weak acid such as oxalic, acetic phosphoric | | |
| Step 5 aldehydes | H or D<br>\|<br>OC—CHR$_6$<br>      \|<br>      A | or   H or D<br>      \|<br>      OC—CH=CH—CH=CHR$_7$ | | |
| | | or   H or D<br>      \|<br>      OC—CH$_2$—CO$_2$R$_8$ | | | where $R_1, R_2, R_3, R_4, R_5, R_6, R_7, R_8$ are methyl, ethyl, propyl, or other alkyl, alkylene, carboalkoxy, or aryl groups having 1 to 12 carbon atoms and A is hydrogen or a phenyl group.

Equation D
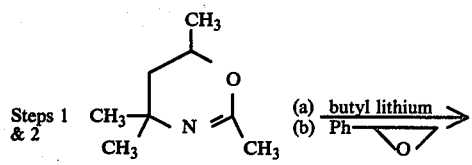
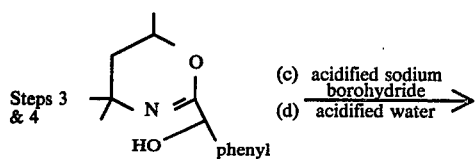
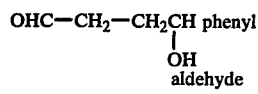
aldehyde
Equation E
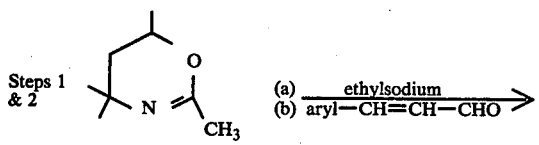
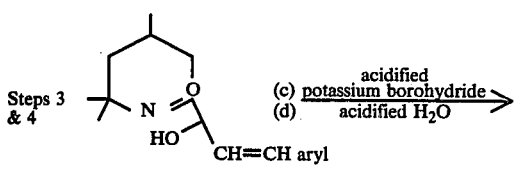
Step 5
aldehydes   OHC—CH=CH—CH=CH-aryl
aryl is phenyl, toluyl, xylyl, benzyl, naphthyl, anthracyl.
Equation F
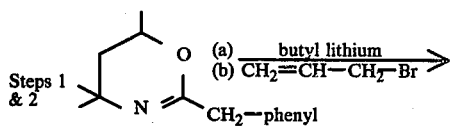
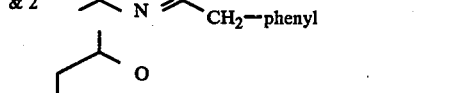
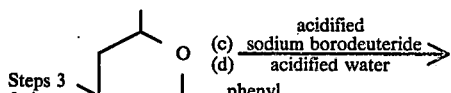
Step 5
aldehyde   OCD—CH—CH$_2$—CHACH$_2$
            |
           phenyl
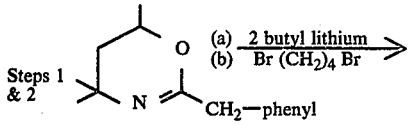
-continued
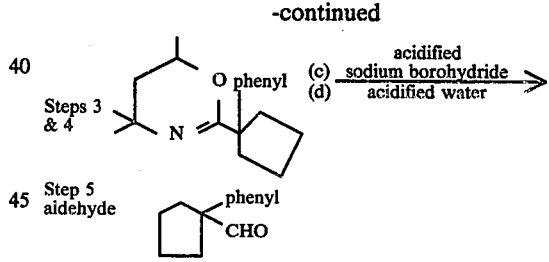
Step 5
aldehyde
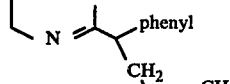
Equation H
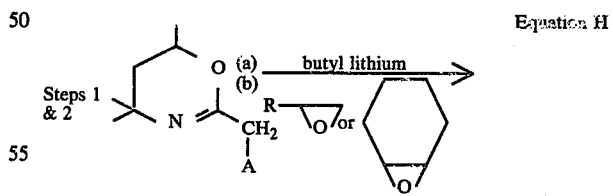
A is hydrogen or phenyl or aryl
R is hydrogen or phenyl or aryl
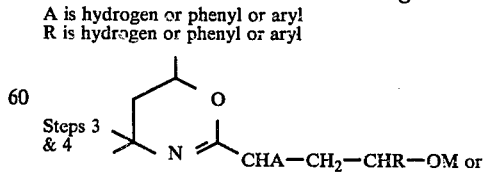
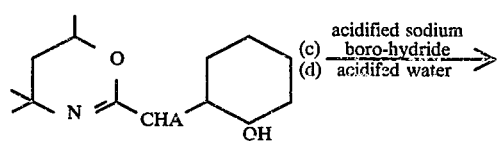

Step 5
aldehydes A
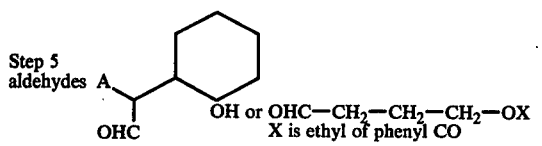
OH or OHC—CH₂—CH₂—CH₂—OX
X is ethyl of phenyl CO or
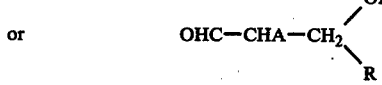
OHC—CHA—CH₂ OH / R The last mentioned R is an alkyl or aryl group having 1-12 carbon atoms. In Step 2, the triangular O sign represents an epoxy derivative of an alkyl or aryl group having 1-12 carbon atoms.

Equation I

Step 1
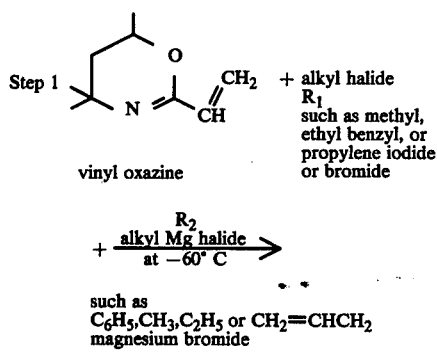
vinyl oxazine
+ alkyl halide
$R_1$
such as methyl, ethyl benzyl, or propylene iodide or bromide $+ \xrightarrow{\text{alkyl Mg halide} \atop \text{at} -60° C} R_2$ such as
$C_6H_5, CH_3, C_2H_5$ or $CH_2=CHCH_2$
magnesium bromide Step 2
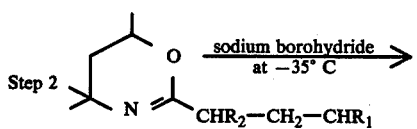
$\xrightarrow{\text{sodium borohydride} \atop \text{at} -35° C}$ Step 3
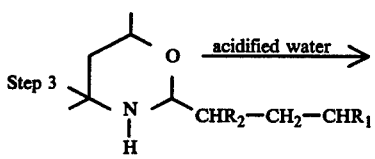
$\xrightarrow{\text{acidified water}}$ Step 4
aldehydes  OCH—CHR₂—CH₂—CHR₁

Equation J

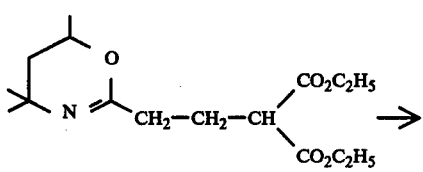
→

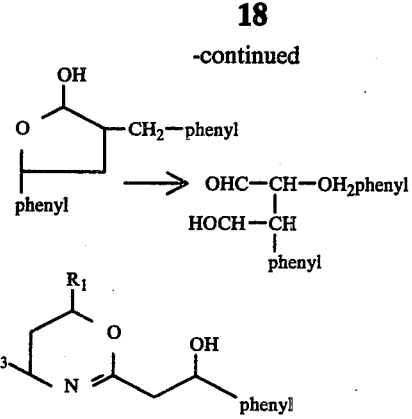

Having now particularly described and ascertained the nature of the invention, and in what manner the same is to be performed, what is claimed is:

1. A process of making aldehydes which comprises reacting a dihydro-1,3-oxazine of the formula

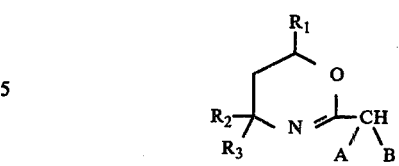

in which $R_1$, $R_2$ and $R_3$ are individually selected from the group consisting of hydrogen, methyl, ethyl and propyl and in which A and B are individually selected from the group consisting of hydrogen, phenyl, cyano, methoxy and carboalkoxy with an alkali metal-alkyl compound below 50° C. to produce an oxazine anion, reacting the anion with an electrophile below −50° C. in an anhydrous organic solvent to produce a dihydrooxazine, treating the dihydrooxazine with an alkali metal borohydride solution at about neutral pH and at subzero temperature to obtain a tetrahydrooxazine, converting the tetrahydrooxazine to the aldehyde by steam distillation or hydrolysis and recovering the aldehyde thus produced.

2. The method of claim 1, the starting oxazine being 2,4,4,6-tetramethyl-5,6dihydro-1,3-oxazine.

3. The method of claim 1, the alkali metal compound being butyllithium.

4. The method of claim 1, the formation of the anion taking place at a temperature of −50° to −78° C in the presence of an anhydrous organic solvent bath.

5. The method of claim 1, the reaction of the anion taking place in an anhydrous tetrahydrofuran solvent solution.

6. The method of claim 1, the reduction taking place at a temperature of between about −10° and −45° C at a pH of 6 to 8 and the alkali metal borohydride being sodium borohydride.

7. The method of claim 1, the alkali metal borohydride being sodium borodeuteride.

8. The method of claim 1, the steam distillation being accomplished from an oxalic acid aqueous bath.

* * * * *